US008636041B2

(12) United States Patent
Yodfat (10) Patent No.: US 8,636,041 B2
(45) Date of Patent: Jan. 28, 2014

(54) METHODS AND DEVICES FOR DELIVERING FLUID TO A RESERVOIR OF A FLUID DELIVERY DEVICE

(75) Inventor: Ofer Yodfat, Maccabim-Reut (IL)

(73) Assignee: Roche Diagnostics Operations Inc., Indianapolis, IN (US)

( * ) Notice: Subject to any disclaimer, the term of this patent is extended or adjusted under 35 U.S.C. 154(b) by 788 days.

(21) Appl. No.: 11/989,680

(22) PCT Filed: Aug. 16, 2007

(86) PCT No.: PCT/IL2007/001027
§ 371 (c)(1),
(2), (4) Date: Jun. 8, 2010

(87) PCT Pub. No.: WO2008/020447
PCT Pub. Date: Feb. 21, 2008

(65) Prior Publication Data
US 2010/0243099 A1    Sep. 30, 2010

Related U.S. Application Data

(60) Provisional application No. 60/838,660, filed on Aug. 18, 2006.

(51) Int. Cl.
*B65B 1/04* (2006.01)
(52) U.S. Cl.
USPC ............. 141/330; 141/23; 141/113; 141/114; 604/414; 604/180
(58) Field of Classification Search
USPC ........... 141/2, 21, 23, 26, 113, 114, 329, 330; 604/414, 180
See application file for complete search history.

(56) References Cited

U.S. PATENT DOCUMENTS 3,722,557 A * 3/1973 Huggins ...................... 141/59
5,526,853 A * 6/1996 McPhee et al. ............... 141/329
(Continued)

FOREIGN PATENT DOCUMENTS

CA    2 170 237 A1    3/1995
EP    1 731 128 A1    12/2006
(Continued)

OTHER PUBLICATIONS

Written Opinion for PCT Application No. PCT/IL2007/001027.
(Continued)

*Primary Examiner* — Jason K Niesz
(74) *Attorney, Agent, or Firm* — Mintz Levin Cohn Ferris Glovsky and Popeo, PC (57) ABSTRACT

Medical devices and methods for delivering therapeutic fluids transcutaneously to a body of a patient via a fluid delivery device and an adapter is provided. A Luer slip connector is provided at a first connecting end of the adapter. A therapeutic fluid container is connected with the second connecting end such that the container's neck is received in the second connecting end and a hollow penetrating member provided in the adapter punctures the septum of the container to admit the therapeutic fluid into a needle-less syringe from the container. After, fluid emerges from the tip of the penetrating member, the second connecting end of the adapter is attached to the fluid delivery device, thereby filling the reservoir with the fluid and pushing the syringe plunger forward to inject fluid into reservoir.

18 Claims, 6 Drawing Sheets

(56) References Cited

U.S. PATENT DOCUMENTS

| | | |
|---|---|---|
| 6,238,372 B1 | 5/2001 | Zinger et al. |
| 6,360,784 B1 * | 3/2002 | Philippens et al. ............... 141/2 |
| 6,379,340 B1 | 4/2002 | Zinger et al. |
| 7,703,486 B2 * | 4/2010 | Costanzo ...................... 141/346 |
| 8,122,923 B2 * | 2/2012 | Kraus et al. .................. 141/329 |
| 2001/0003996 A1 * | 6/2001 | Jansen et al. .................. 141/329 |
| 2002/0127150 A1 | 9/2002 | Sasso |
| 2003/0032935 A1 | 2/2003 | Damiano et al. |
| 2005/0021000 A1 | 1/2005 | Adair et al. |
| 2005/0131357 A1 | 6/2005 | Denton et al. |
| 2007/0106218 A1 | 5/2007 | Yodfat et al. |
| 2008/0119792 A1 * | 5/2008 | Kornerup et al. ........ 604/164.01 |

FOREIGN PATENT DOCUMENTS

| | | |
|---|---|---|
| WO | WO 00/35517 A1 | 6/2000 |
| WO | WO 2005/074860 A1 | 8/2005 |
| WO | WO 2007/015233 A1 | 2/2007 |

OTHER PUBLICATIONS

Communication for Corresponding European Application No. 07805487.1, dated Nov. 3, 2009.

Communication for Corresponding European Application No. 07805487.1, dated Nov. 4, 2009.

International Search Report, PCT Application No. PCT/IL2007/001027, date of mailing Dec. 21, 2007.

* cited by examiner

METHODS AND DEVICES FOR DELIVERING FLUID TO A RESERVOIR OF A FLUID DELIVERY DEVICE

CROSS REFERENCE TO RELATED APPLICATIONS

This application is a national stage entry of PCT/IL07/001027, having an international filing date of Aug. 16, 2007, which claims priority to U.S. provisional patent application No. 60/838,660, filed Aug. 18, 2006. Each of the foregoing disclosures is expressly incorporated herein in its entirety.

FIELD OF THE INVENTION

Embodiments of the present invention relate to medical devices, and more particularly to medical devices for delivering therapeutic fluids transcutaneously to a body of a patient, e.g. infusion pumps, disposable infusion pumps, etc.

BACKGROUND OF THE INVENTION

Prior art devices to facilitate transfer of a dose of a fluid from a bulk container are well known in the art. Usually, these devices are used to transfer a dose of a medicament from a vial or a bulk container of a medicament into a syringe for injection or administrating the dose to a patient. Examples of such devices are documented in U.S. Pat. Nos. 6,238,372 and 6,379,340 to Zinger. More advanced adapters, as documented in U.S. Patent Application Publication No. 2005/0131357 to Denton, are capable of receiving several discharge orifices.

U.S. Patent Application Publication No. 2005/0021000 to Adair et al. discloses an adapter for connecting between a reservoir, a syringe, infusion set tubing, and an infusion pump. According to this disclosure, the reservoir is a detachable component, which is first filled using the adapter and is later inserted into the infusion pump.

Accordingly, the prior art adapters are generally suitable for use between a syringe and vial or other medicament container, which has an orbicular neck. Such devices are not suitable for the filling of fluid infusion devices which have a non-orbicular end at which is disposed an inlet port for filling reservoir of the fluid infusion device, as disclosed in Israel Patent Application No. 171813 and U.S. patent application Ser. No. 11/397,115.

Specifically, due to the miniature size of such infusion devices, it is often difficult for a patient to locate and pierce the seal covering the orifice of the fluid reservoir. Furthermore, the use of unshielded needle to pierce the medicament container septum or the sealed orifice of the reservoir might be associated with inadvertent punctures.

SUMMARY OF THE EMBODIMENTS

Embodiments of the present invention address the above-noted concerns and provide methods and apparatuses to allow the filling of the reservoir of an infusion device having a non-orbicular end, with a medicament fluid withdrawn from a medicaments fluid container. Such methods and apparatuses may be used with small, low-cost, portable infusion devices/systems comprising disposable and reusable parts. Examples of such devices can be found in Israel Patent Application No. 171813, and U.S. patent application Ser. No. 11/397,115, filed Apr. 3, 2006, both disclosures of which are herein incorporated by reference in their entirety.

According to some embodiments of the present invention, such methods and devices are designed and manufactured to be inexpensive and preferably eliminate the occurrence of punctures associated with using unshielded needles.

According to some embodiments of the present invention, an adapter for establishing fluid communication between a syringe and a medicament container, and/or between a syringe and reservoir of a fluid infusion device are provided. Such an adapter is preferably intended for withdrawal of medicament fluid from a container and filling the reservoir within the disposable part of the infusion device with the extracted fluid.

In an embodiment of the present invention, the adapter may include an elongated body made of a medical plastic and consisting of two opposite connecting ends. A fluid communication is enabled between the first connecting end and the second connecting end via a hollow needle or sharpened cannula.

In an embodiment of the present invention, the first connecting end may be provided with a cavity adapted to receive a male half connector (e.g., Luer slip connector) of a needle less syringe. The cavity is in fluid communication with the second end via a hollow piercing member, which can be either a needle provided in a female half of the connector (e.g., Luer slip connector) or a sharpened cannula secured in the cavity so as to extend therefrom towards the second connecting end.

In an embodiment of the present invention, the second connecting end may include a depression, which is adapted to receive therein at least one of an outlet of a therapeutic fluid container (e.g., an orbicular neck), and an inlet (e.g., a non-orbicular end) of the housing of a fluid infusion device (e.g., the disposable part). The second connecting end may also be provided with an abutment wing, which may be configured and dimensioned to support the adapter against the housing wall after the adapter has been attached to the housing.

In an embodiment of the present invention, the piercing member may be used to pierce either the sealing cover of a therapeutic fluid container or the sealing cover of the reservoir of the fluid infusion device.

According to some embodiments of the present invention, a method for filling a reservoir of a fluid delivery device is provided. The method includes connecting a male half of a connector of a needle-less syringe to the first connecting end, pushing a syringe's plunger to a protracted position, connecting a medicament fluid container with the second connecting end such that the container's outlet is received in the second connecting end and the piercing member punctures the outlet (e.g., septum) of the container to admit the fluid into syringe from the container, pulling the syringe's plunger (preferably while holding the syringe in a vertical position) whereas the medicament container is preferably on top (e.g., at a higher vertical level), to permit the withdrawal of the fluid from the container to the syringe, and detaching the medicament fluid container from the second connecting end. Further, some of the embodiments includes the priming of air from the syringe by holding the syringe in a vertical position while the second connecting end is on top (at a higher vertical position) and slightly pushing the plunger until a first drop(s) of fluid emerges from the tip of the piercing member. In addition, some methods may include attaching the second connecting end of the adapter to the housing of disposable part of the fluid infusion device so as to enable the piercing member to puncture the seal which covers the orifice of the reservoir, to admit the fluid into reservoir from the syringe. The reservoir may be filled with the fluid by holding the assembly in a vertical position, whereas the exit port of the disposable part is preferably on top (e.g., at a higher vertical position), and pushing the syringe plunger forward and inject fluid into reservoir, until a first drop(s) of medicament fluid emerges from the exit port of the fluid infusion device. The adapter is thereby detached from the disposable part of the fluid infusion device.

The foregoing and other features, aspects, and advantages of the present invention will be more apparent from the following detailed description, which illustrates exemplary embodiments of the present invention.

BRIEF DESCRIPTION OF THE DRAWINGS

For a better understanding of the present invention, reference is made to the following description, taken in conjunction with the accompanying drawings, in which like reference characters refer to like parts throughout, and in which.

DETAILED DESCRIPTION OF THE INVENTION

The foregoing and other features, aspects, and advantages of the present invention will be more apparent from the following detailed description, which illustrates exemplary embodiments of the present invention.

Figure 1:
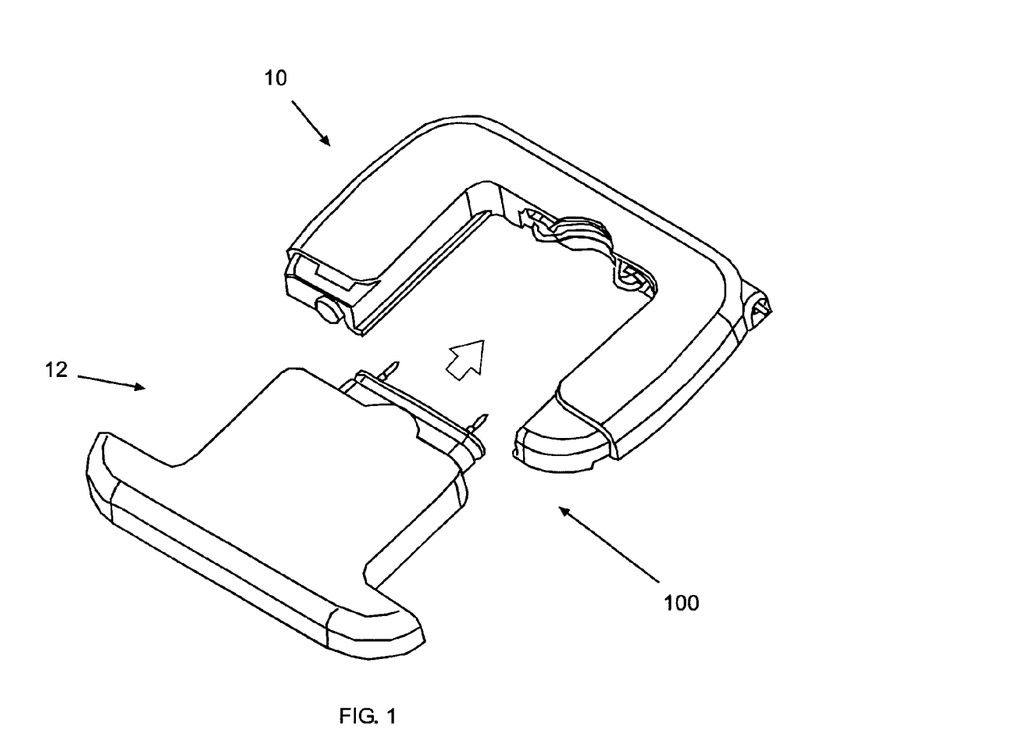
FIG. 1 is a perspective view of a fluid delivery device in accordance with some embodiments of the present invention.

Referring now to FIG. 1, there is illustration of an exemplary embodiment of a fluid delivery device 100 constructed in accordance with some of the embodiments of the present invention, also referred to as a patch unit, which may be adherable to a patient's body, and a remote control unit (not shown), which communicates with the patch unit 100. The patch unit may comprise a disposable portion 10, which is detachably connectable to a reusable portion 12. The configuration of the fluid delivery device comprising such a patch unit is disclosed in Applicants Israel Patent Application No. 171813 as well as in U.S. patent application Ser. No. 11/397,115, both disclosures herein incorporated by reference in their entireties.

One of the advantageous of such a fluid delivery device 100 configuration is that the relatively expensive components may be deployed within the reusable portion 12 while less expensive components might be accommodated within the disposable portion 10. By virtue of this provision, the use of the device is significantly more economical for the patient.

Figure 2:
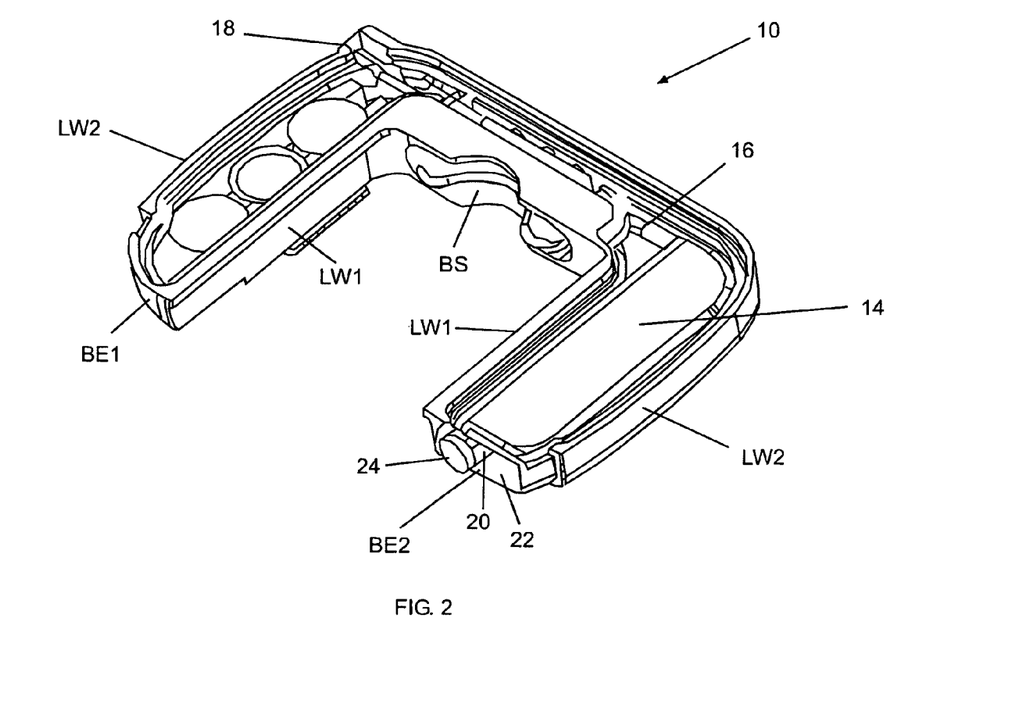
FIG. 2 is a fragmented perspective view of the fluid delivery device detailing the reusable portion in accordance with some embodiments of the present invention.

Reusable portion 12 of a fluid delivery device 100 may be removably coupled to a disposable portion 10 in operative association, as shown in FIG. 1. In FIG. 2, only the disposable portion 10 of the fluid delivery device is shown. The disposable portion 10 may include a U-shaped housing defined by lateral walls LW1 and LW2, by bridging section BS and by butt ends BE1 and BE2. One of ordinary skill in the art would recognize that the U-shaped housing may vary in shape in perspective to a non-formal U-shape. Additional components of the disposable portion 10 may include a reservoir 14 situated between lateral walls and butt end BE2. The reservoir 14 preferably includes a therapeutic fluid, e.g. insulin. The reservoir 14 is in fluid communication with a delivery tube 16, terminating by an outlet port 18. Through this port the fluid can be delivered to a cannula (not shown), which is subcutaneously inserted in a patient.

The reservoir 14 can be filled with the therapeutic fluid through an inlet port 20, which may be made in butt end BE2. The butt end BE2 may include a rectangular configuration terminating by a face 22. A sealing cover 24 preferably seals the inlet port 20.

In accordance with the design of the patch fluid delivery device unit 100, a portion of the delivery tube 16, which extends along the bridging section BS may be placed between a stator plate and wheels of a peristaltic pump of the reusable portion 12 (not shown). When these wheels rotate, they depress the tube 16 to the plate and squeeze it. Accordingly, the fluid is periodically pumped from the reservoir 14 to exit port 18 and further to the cannula.

Figure 3:
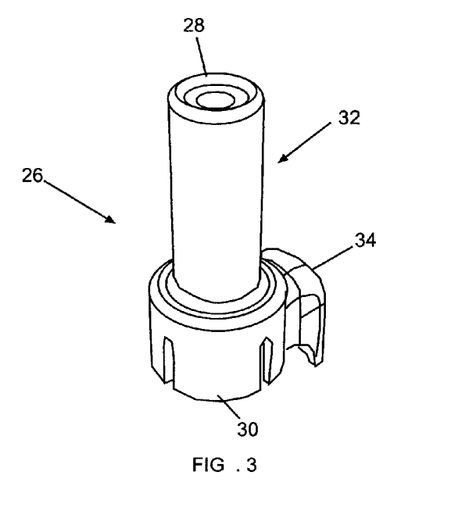
FIG. 3 is perspective side view of an adapter in accordance with some embodiments of the present invention.
Figure 4:
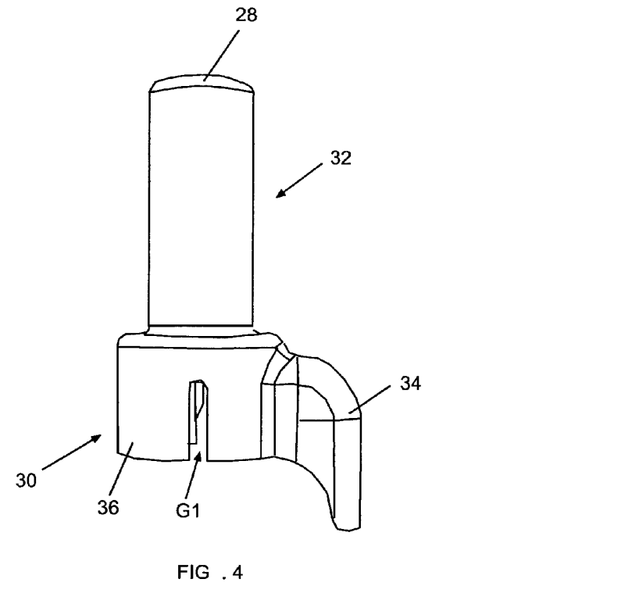
FIG. 4 is a side view of the adapter of FIG. 3 in accordance with some embodiments of the present invention.
Figure 5:
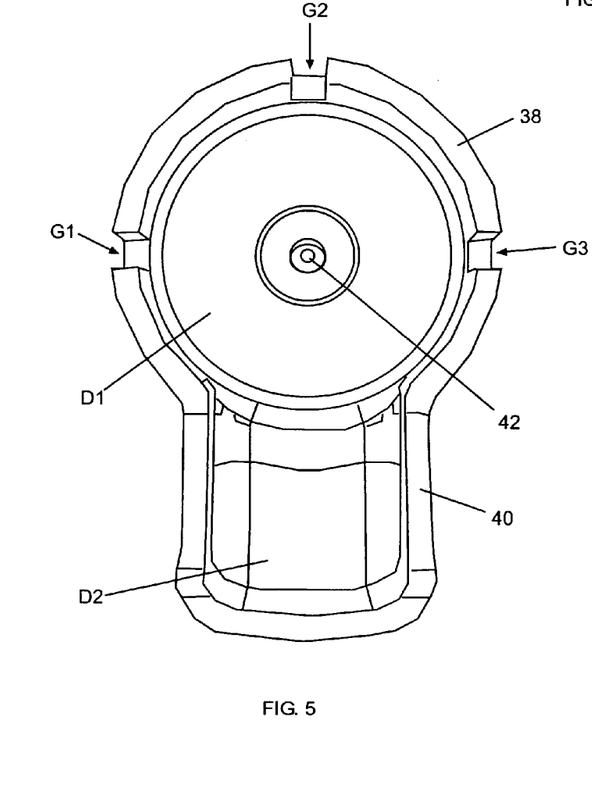
FIG. 5 is a bottom view of the adapter of FIG. 3 in accordance with some embodiments of the present invention.
Figure 8:
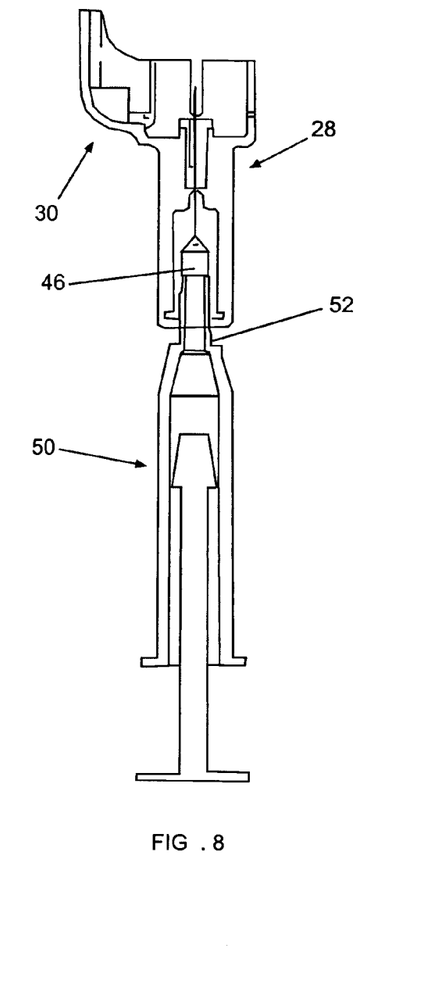
FIG. 8 is a side, cross-sectional view of the adapter connecting to a needle-less syringe in accordance with some embodiments of the present invention.

With reference to FIGS. 3-5 adapter 26 of the invention is generally illustrated, which may be suitable for connecting the reservoir 14 with a syringe filled with a therapeutic fluid. Preferably, the adapter 26 is configured as an elongated tubular structure made of a plastic suitable for medical use, which in a preferred embodiment is of inexpensive material. The adapter 26 may include a first connecting end 28, and may also include an opposite second connecting end 30, with an intermediate body portion 32. The first connecting end 28 may be attachable to a needle-less syringe 50, as seen in FIG. 8. The second connecting end 30 may be releasably attachable either to a circular neck of container for therapeutic fluid or to an end (e.g., rectangular butt end BE2) of a housing of a fluid delivery device (e.g., that of the patch unit 100).

The second connecting end 30 may be provided also with an abutment wing 34, which may be used to rest on lateral wall LW2 of the housing when the second connecting end 30 is connected to the butt end BE2 of the housing.

Referring to FIGS. 4 and 5, it is seen that the second connecting end 30 may be provided with a border wall 36 delimiting a depression. The contour of the border wall 36 comprises a circular portion 38 and a non-circular portion 40. The non-circular portion 40 may be a rectangular shape or any other shape which would be understood by one of ordinary skill in the art. The circular portion 38 of the border wall 36 may define a circular region D1 of the depression. This region D1 is preferably intended for receiving the circular neck of the fluid container. The non-circular portion 40 of the border wall may define a non-circular region D2 of the depression. This region D2 can be used for receiving butt end BE2 of the housing. The circular 38 and non-circular 40 regions may be configured and dimensioned to allow a tight fit with the received items irrespective whether it is circular neck of the fluid container or butt end of the housing.

Circular portion of the border wall is provided with gaps G1, G2, G3, to provide a discontinuous arrangement, which preferably provides a degree of elasticity. It is understood by one of ordinary skill in the art that the number of gaps G1-G3 may vary accordingly between alternative embodiments. Seen in the center of the region D1 is a sharpened end 42 of a penetrating member, which is secured at the first connecting end of the adaptor 26.

The sharpened end is preferably fully concealed within depression delimited by the border wall 36 and therefore is preferably not accessible. By virtue of this provision inadvertent puncture may be prevented.

Figure 6:
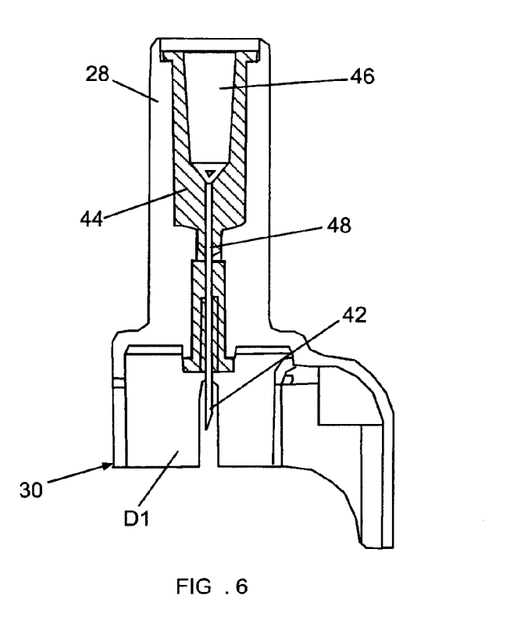
FIG. 6 is a side, cross-section view of the adapter of FIG. 3 in accordance with some embodiments of the present invention.

As shown in FIG. 6, the first connecting end 28 may be provided with a core 44, in which a cavity 46 may be provided. The shape of the core and of the cavity may be selected to constitute a female half of Luer slip connector. A hollow penetrating member 48 is secured within the core such that sharp end 42 of the penetrating member protrudes inside region D1 of the depression made in the second connecting end 30 of the adapter 26. By virtue of this provision, fluid communication is provided between cavity 46 and the depression in the second connecting end 30. As a suitable penetrating member, one can use a hollow needle or a cannula, according to one embodiment. Instead of dedicated core with cavity 46, one can use ready-to-use female half of Luer connector, which would be suitably embedded in the first connecting end 28.

Figure 7:
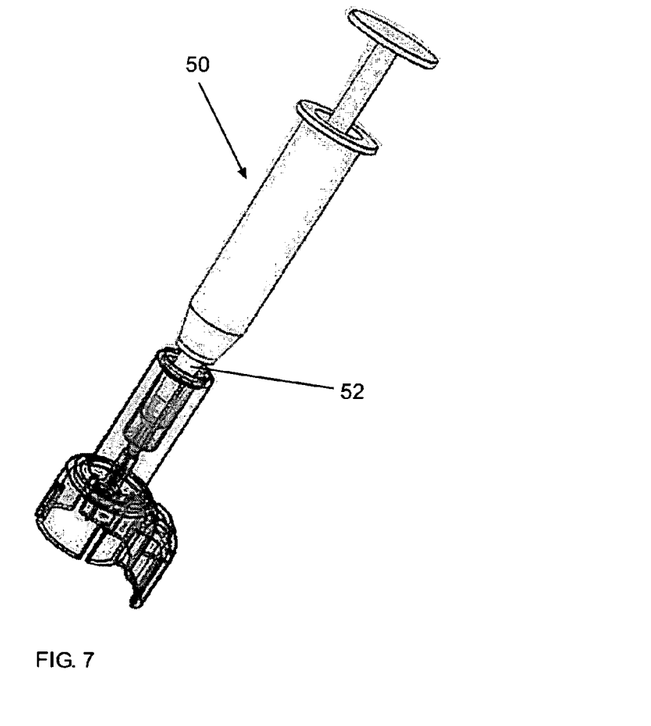
FIG. 7 is a side, cross-sectional view of an adapter connecting to a needle-less syringe in accordance with some embodiments of the present invention.

Referring to FIGS. 7 and 8 it is shown how a needle-less syringe 50 is connected to the first connecting end 28 of the adapter 26. It is seen that male half 52 of Luer slip connector provided at the syringe 50 is inserted within female half 46 of the Luer connector associated with the first connecting end 28.

Figure 9A:
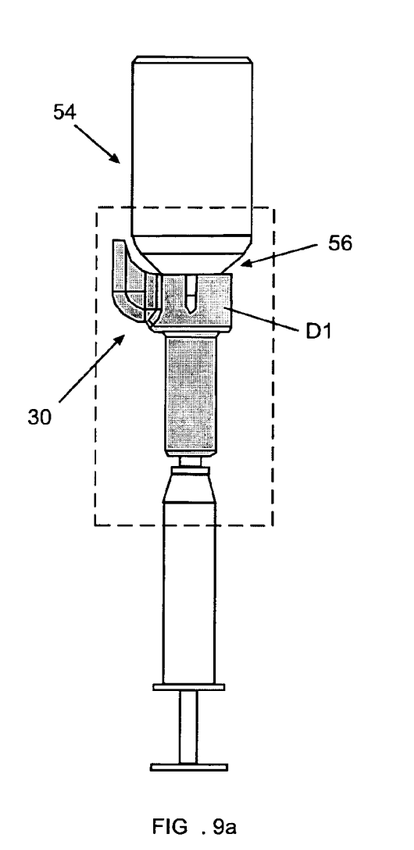
FIG. 9A is a side view of an adapter attached to a fluid container and a syringe in accordance with some embodiments of the present invention.
Figure 9B:
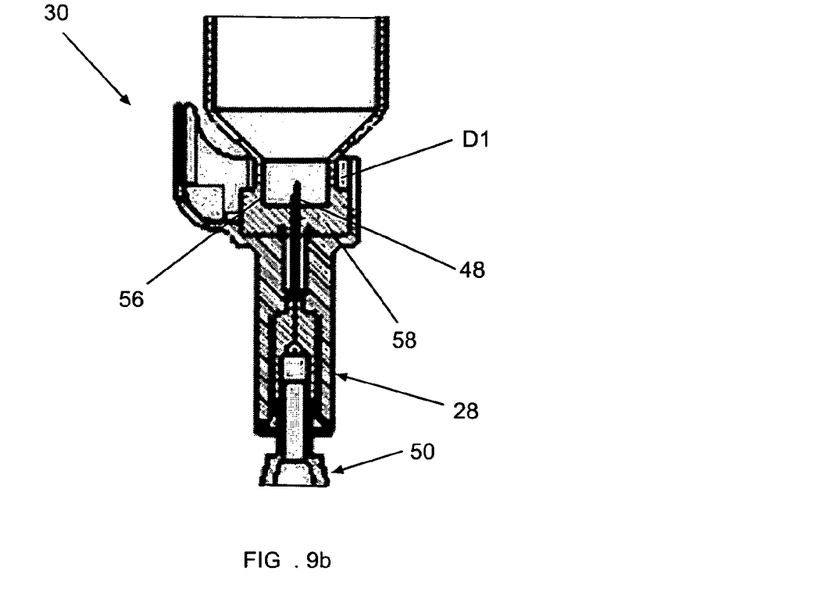
FIG. 9B is a side, partial, cross-sectional view of the adapter attached to the fluid container and syringe of FIG. 9A.

Referring to FIGS. 9A and 9B it is shown how the second connecting end 30 may be attached to a fluid container 54. It is seen in FIG. 9b, that when a neck 56 of the container is fully received within circular depression region D1 of the second connecting end 30, the penetrating member 48 pierces a cover 58 of the container and protrudes inside the container. One of skill in the art can readily appreciate that since there is provided fluid communication between the first 28 and second 30 connecting ends, the therapeutic fluid could be withdrawn from the container through the penetrating member into the syringe 50.

Figure 10A:
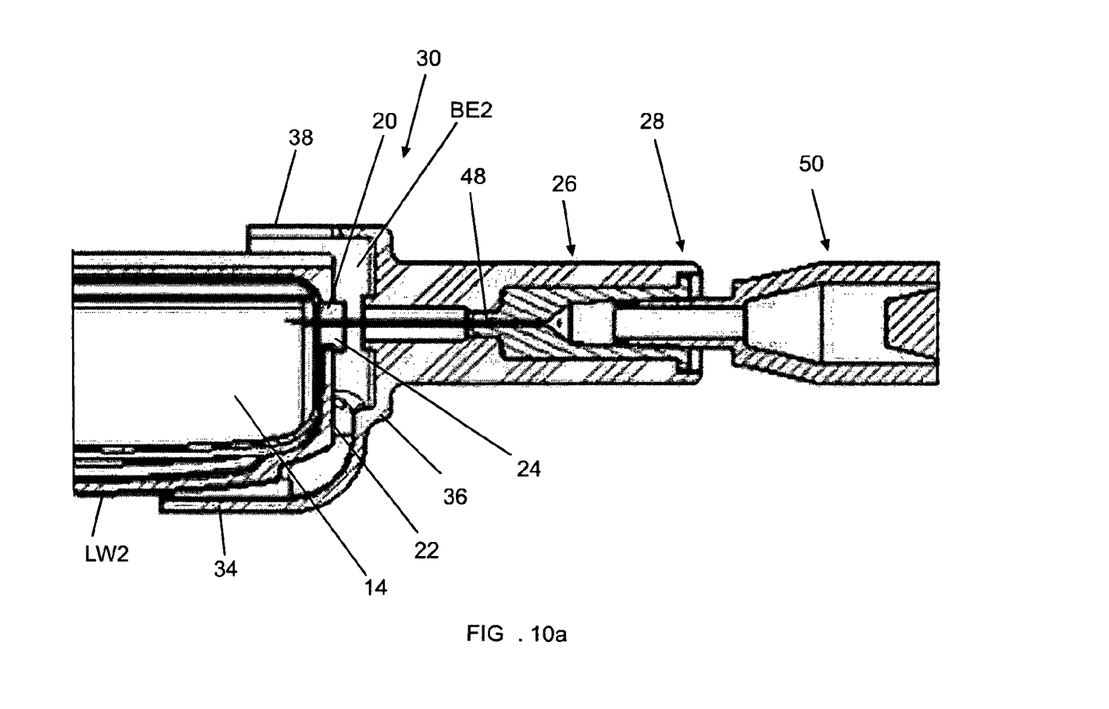
FIG. 10A is a top view of the assembly of a fluid delivery device, an adapter and a syringe in accordance with some embodiments of the present invention.
Figure 10B:
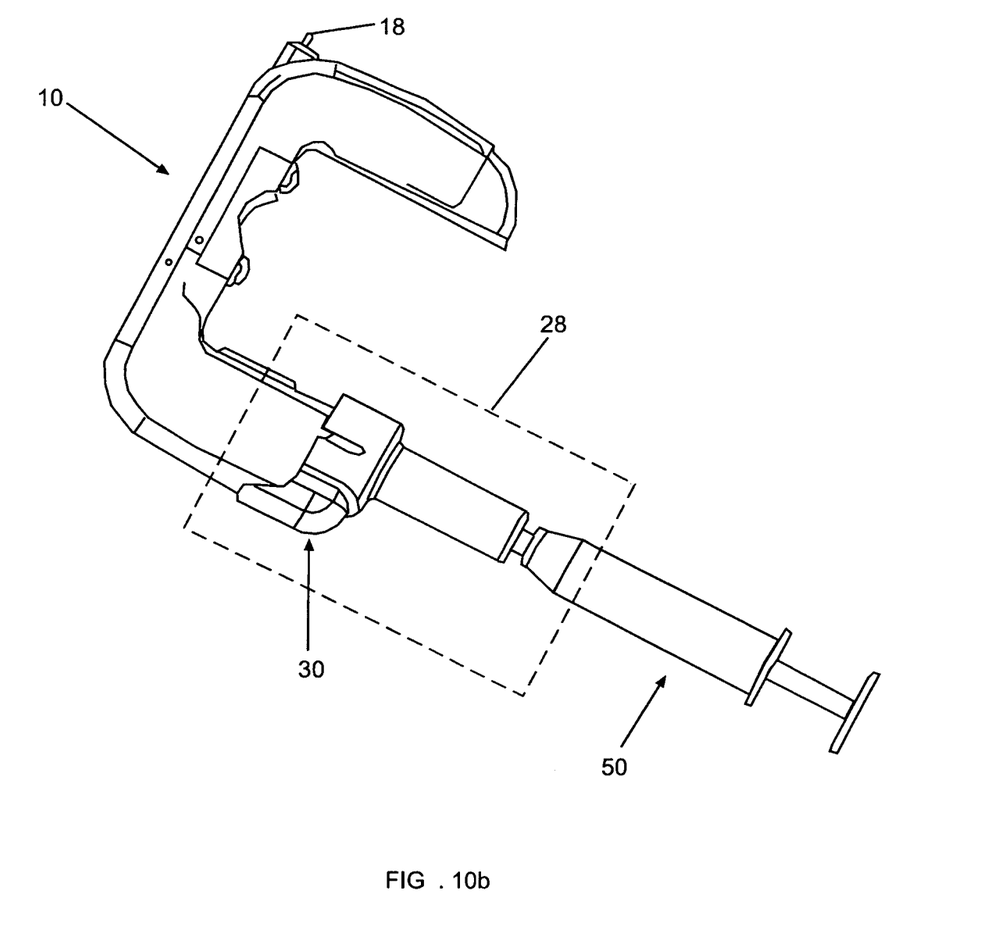
FIG. 10B is a cross-sectional, side view of a portion of the assembly shown in FIG. 10A, in accordance with some embodiments of the present invention.

Referring now to FIGS. 10a and 10b it is shown the second connecting end 30 of the adapter 26 being attached to rectangular butt end BE2 of the housing, while first connecting end 28 is attached to syringe 50 such that reservoir 14 can be filled or replenished by the therapeutic fluid from the syringe 50.

It is seen that the butt end BE2 is received within depression in the second connecting end 30 such that it is embraced by non-circular portion 38 of the border wall and by abutment wing 34 juxtaposed with lateral wall LW2 of the housing. In this position piercing member 48 pierces sealing cover 24 of the reservoir 14 such that therapeutic fluid can be delivered through inlet port 20 to the reservoir from syringe 50.

Below is an exemplary method, according to some embodiments of the present invention, of how a reservoir of a fluid infusion device can be filled with the aim of adapter of the invention.

When filling the reservoir of the fluid infusion device, the first connecting end of the adapter may be attached to the male half of Luer connector of a needle-less regular syringe as illustrated in FIG. 7. Typically, such syringes are supplied with separate therapeutic fluid containers in a pharmacy store. The second connecting end of the adapter may then be firmly attached to the fluid container until circular portion of the border wall engages the orbicular neck of the fluid container and piercing member pierces sealing cover of the container.

In one embodiment, in order to eliminate entering of air into syringe, the syringe connected to adapter is held in a vertical position whereas the second connecting end is on top, as illustrated in FIG. 8A. By pulling the syringe's plunger backward, fluid from the container can be withdrawn through the piercing member into the syringe.

When the syringe is filled with the desired dose, the fluid container is detached from the second connecting end.

It is worth noting that entrapment of air bubbles during the withdrawing process should preferably be prevented. For this purpose, according to an embodiment of the invention, air is primed from the syringe before withdrawal of the medicament fluid. During the priming, the syringe is preferably held in a vertical position whereas the second connecting end is on top. Then, the plunger of the syringe may be slightly pushed inwardly until a first drop(s) of the fluid appears at the tip of the penetrating member.

After the syringe is filled with the fluid, the second connecting end of the adapter may be separated from the container and then attached to the housing of the disposable portion of the fluid infusion device as illustrated in FIG. 10A and FIG. 10B. The therapeutic fluid can be now transferred from the syringe to the reservoir of the fluid infusion device. It is worth noting that during attachment and filling of the reservoir, the adapter and the housing are preferably held in a vertical position such that the outlet port of the housing is on top. Then, the plunger may be slowly pushed inwardly until first drop(s) of fluid appears at the outlet port, indicating that reservoir is full and that air in delivery tube was primed.

The adapter can then be detached from the housing and the fluid infusion device is ready to operate.

Although particular embodiments have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the invention as defined by the claims. Other aspects, advantages, and modifications are considered to be within the scope of the following claims. The claims presented are representative of the inventions disclosed herein. Other, unclaimed inventions are also contemplated. The applicant reserves the right to pursue such inventions in later claims.

What is claimed is:

1. An adapter device for enabling the transfer of fluid to a reservoir of a fluid delivery device comprising:
    an intermediate body portion;
    a first connecting end at one end of the body portion configured to connect to a connector of a needle-less syringe;
    a second connecting end at an opposite end of the body portion, the second connecting end being configured to be non-simultaneously attachable to a container of a therapeutic fluid and a housing of a fluid delivery device; and
    a hollow penetrating member deployed within a core of the first connecting end, said penetrating member being provided with a sharp end which protrudes inside the second connecting end;
    wherein the second connecting end defines a depression configured to receive non-simultaneously at least an outlet of the container and an end of the housing of the fluid delivery device; and wherein the second connecting end is provided with a border wall that delimits the depression, the depression having:
- a circular portion defining a circular region of the depression intended for receiving at least a portion of a circular neck of the fluid container; and
- a non-circular portion defining a non-circular region intended for receiving at least a portion of the end of the housing.

2. The adapter device of claim 1, wherein the hollow penetrating member is a needle.

3. The adaptor device of claim 1, wherein at least a part of the core is configured as a female half of a slip connector.

4. The adapter device of claim 1, wherein the hollow penetrating member is a sharpened cannula.

5. The adapter device of claim 1, wherein the second connecting end further comprises an abutment wing configured to support the adapter device against a housing wall when attaching the adapter device to the housing.

6. The adapter device of claim 1, wherein the hollow penetrating member is capable of piercing at least one of a sealing cover of the therapeutic fluid container and a sealing cover of the a reservoir of the fluid delivery device.

7. The adapter device of claim 6, wherein the fluid delivery device includes a reusable portion coupled to a disposable portion.

8. The adapter device of claim 7, wherein the disposable portion comprises a U-shaped housing defined by a plurality of lateral walls, a bridging section; and two butt ends, wherein each butt end has a rectangular configuration.

9. The adapter device of claim 8, wherein the reservoir is situated between two of the lateral walls and one of the butt ends, wherein the reservoir is capable of containing a therapeutic fluid.

10. The adapter device of claim 6, wherein the fluid delivery device is adherable to a body of a patient.

11. The adapter device of claim 9, wherein the second connecting end is provided with a border wall that delimits said depression, said depression having:
- a circular portion defining a circular region of the depression intended for receiving
- at least a portion of a circular neck of the fluid container; and
- a non-circular portion defining a non-circular region intended for receiving at least a portion of the one of the two butt ends of the housing.

12. The adapter device of claim 11, wherein the circular portion of the border wall defines a plurality of gaps.

13. A method for filling a reservoir of a fluid delivery device, comprising:
- providing a fluid delivery device;
- providing an adapter, wherein the adapter comprises:
  - an intermediate body portion comprising a hollow penetrating member,
  - a first connecting end at one end of the intermediate body portion, the first connecting end comprising a female half of a connector for connection to a male half of a needle-less syringe, and
  - a second connecting end at an opposite end of the intermediate body portion, the second connecting end being provided with a border wall that delimits a depression having a circular portion defining a circular region of the depression intended for receiving at least a portion of a circular neck of the fluid container, and a non-circular portion defining a non-circular region intended for receiving at least a portion of an end of the housing;
- connecting the male half of the connector of the needle-less syringe to the first connecting end;
- pushing a plunger of the needle-less syringe to a protracted position;
- connecting a therapeutic fluid container with the second connecting end such that the container's outlet is received in the second connecting end of the adapter and the hollow penetrating member punctures the container's outlet to admit the fluid into the syringe from the container;
- pulling the syringe's plunger to a retracted position to fill the syringe at least partially with the fluid from the container;
- detaching the therapeutic fluid container from the second connecting end of the adapter;
- attaching the second connecting end of the adapter to a housing of the fluid delivery device so that the hollow penetrating member punctures a seal which covers an orifice of the reservoir to admit the therapeutic fluid into reservoir from the needle-less syringe; and
- pushing the needle-less syringe plunger forward to inject the therapeutic fluid into reservoir until at least a drop of therapeutic fluid emerges from an exit port of the fluid delivery device.

14. The method of claim 13, further comprising detaching the adapter from the fluid delivery device.

15. The method of claim 13, comprising holding the therapeutic fluid container at a higher level to permit the withdrawal of the therapeutic fluid from the container to the needle-less syringe when the needle-less syringe's plunger is pulled in the retracted position.

16. The method of claim 13, further comprising priming the needle-less syringe with the fluid and purge any air from the needle-less syringe, including holding the needle-less syringe in a vertical position while the second connecting end is at a higher level.

17. The method of claim 13, wherein the detachment of the therapeutic fluid container from the second connecting end of the adapter occurs upon the needle-less syringe being filled at a predetermined amount.

18. An adapter device for enabling the transfer of fluid to a reservoir of a fluid delivery device comprising:
- an intermediate body portion;
- a first connecting end at one end of the body portion configured to connect to a connector of a needle-less syringe;
- a second connecting end at an opposite end of the body portion, the second connecting end being configured to be non-simultaneously attachable to a container of a therapeutic fluid and a housing of a fluid delivery device; and
- a hollow penetrating member deployed within a core of the first connecting end, said penetrating member being provided with a sharp end which protrudes inside the second connecting end;

wherein:
- the second connecting end defines a depression configured to receive non-simultaneously at least an outlet of the container and an end of the housing of the fluid delivery device;
- the hollow penetrating member is capable of piercing at least one of a sealing cover of the therapeutic fluid container and a sealing cover of the a reservoir of the fluid delivery device;
- the fluid delivery device includes a reusable portion coupled to a disposable portion;

the disposable portion comprises a U-shaped housing defined by a plurality of lateral walls, a bridging section; and two butt ends, wherein each butt end has a rectangular configuration;

the reservoir is situated between two of the lateral walls and one of the butt ends, wherein the reservoir is capable of containing a therapeutic fluid;

the fluid delivery device is adherable to a body of a patient;

the second connecting end is provided with a border wall that delimits said depression, said depression having:
  a circular portion defining a circular region of the depression intended for receiving at least a portion of a circular neck of the fluid container; and
  a non-circular portion defining a non-circular region intended for receiving at least a portion of the one of the two butt ends of the housing.

* * * * *

UNITED STATES PATENT AND TRADEMARK OFFICE
CERTIFICATE OF CORRECTION

PATENT NO. : 8,636,041 B2  
APPLICATION NO. : 11/989680  
DATED : January 28, 2014  
INVENTOR(S) : Ofer Yodfat It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1266 days.

Signed and Sealed this
Twenty-second Day of September, 2015

Michelle K. Lee
*Director of the United States Patent and Trademark Office*